(12) United States Patent
Nix et al.

(10) Patent No.: US 8,819,928 B2
(45) Date of Patent: Sep. 2, 2014

(54) ULTRASONIC IMAGING CATHETERS

(75) Inventors: Elvin Nix, Gold River, CA (US); William Howes, London (GB); Robert Dickinson, London (GB); Stephan Wnendt, Aachen (DE)

(73) Assignee: Volcano Corporation, San Diego, CA (US)

( * ) Notice: Subject to any disclaimer, the term of this patent is extended or adjusted under 35 U.S.C. 154(b) by 303 days.

(21) Appl. No.: 12/844,023

(22) Filed: Jul. 27, 2010

(65) Prior Publication Data
US 2011/0010925 A1 Jan. 20, 2011

Related U.S. Application Data

(60) Division of application No. 11/413,730, filed on Apr. 28, 2006, now Pat. No. 7,762,954, which is a continuation of application No. 10/333,099, filed as application No. PCT/GB01/03262 on Jul. 20, 2001, now Pat. No. 7,037,269.

(30) Foreign Application Priority Data

Jul. 20, 2000 (GB) .................................. 0017674.3

(51) Int. Cl.
| | |
|---|---|
| H05K 3/00 | (2006.01) |
| A61B 8/00 | (2006.01) |
| A61B 8/12 | (2006.01) |
| A61B 1/00 | (2006.01) |
| A61F 2/958 | (2013.01) |
| A61M 25/10 | (2013.01) |
| A61F 2/88 | (2006.01) |
| A61B 5/00 | (2006.01) |

(52) U.S. Cl.
CPC ........ *A61F 2/958* (2013.01); *A61M 2025/1093* (2013.01); *A61F 2/88* (2013.01); *A61B 8/4488* (2013.01); *A61B 8/12* (2013.01); *A61B 1/00082* (2013.01); *A61B 5/4839* (2013.01); *A61F 2250/0068* (2013.01); *A61M 25/104* (2013.01)
USPC .................. 29/829; 29/594; 29/832; 29/846; 600/437; 600/466; 73/625; 310/334; 601/2

(58) Field of Classification Search
USPC .................... 29/594, 829, 832, 846; 600/437, 600/466–471; 73/625, 626; 310/334, 336; 601/2, 3
See application file for complete search history.

(56) References Cited

U.S. PATENT DOCUMENTS 5,109,861 A * 5/1992 Walinsky et al. ............. 600/463
5,163,445 A 11/1992 Christian et al.

(Continued)

FOREIGN PATENT DOCUMENTS

| EP | 0621017 | 10/1994 |
|---|---|---|
| EP | 0554082 | 12/1997 |

(Continued)

OTHER PUBLICATIONS

International Search Report.

(Continued)

*Primary Examiner* — Peter DungBa Vo
*Assistant Examiner* — Jeffrey T Carley
(74) *Attorney, Agent, or Firm* — Haynes and Boone, LLP

(57) ABSTRACT

An intravascular ultrasonic imaging catheter is provided with a flexible circuit electrically coupled to a transducer array mounted on the distal end of the catheter, a portion of the flexible circuit being helically wound about the catheter in order to enhance the flexibility of the circuit. The catheter may be a balloon catheter which is also provided with a stent mounted on the balloon, the stent carrying one or more drugs designed to be eluted or washed into a patient's blood stream after the stent has been delivered, by a the balloon catheter, into a target area within the patient's vascular system.

16 Claims, 4 Drawing Sheets

(56) References Cited

U.S. PATENT DOCUMENTS

| | | | |
|---|---|---|---|
| 5,240,004 A * | 8/1993 | Walinsky et al. | 600/467 |
| 5,243,988 A * | 9/1993 | Sieben et al. | 600/463 |
| 5,257,629 A | 11/1993 | Kitney et al. | |
| 5,259,837 A * | 11/1993 | Van Wormer | 604/103.1 |
| 5,398,689 A | 3/1995 | Connor et al. | |
| 5,603,327 A * | 2/1997 | Eberle et al. | 600/467 |
| 5,876,345 A | 3/1999 | Eaton et al. | |
| 5,971,955 A * | 10/1999 | Nap et al. | 604/101.05 |
| 6,246,898 B1 | 6/2001 | Vesely et al. | |
| 6,283,921 B1 | 9/2001 | Nix et al. | |
| 6,618,916 B1 * | 9/2003 | Eberle et al. | 29/25.35 |
| 6,712,767 B2 * | 3/2004 | Hossack et al. | 600/467 |
| 6,726,677 B1 | 4/2004 | Flaherty et al. | |
| 2002/0002371 A1 * | 1/2002 | Acker et al. | 606/27 |
| 2003/0199747 A1 | 10/2003 | Michlitsch et al. | |

FOREIGN PATENT DOCUMENTS

| | | |
|---|---|---|
| GB | 2287375 | 9/1995 |
| WO | WO 98/02096 | 1/1998 |
| WO | WO 99/16500 | 4/1999 |

OTHER PUBLICATIONS

PCT International Preliminary Examination Report.

* cited by examiner

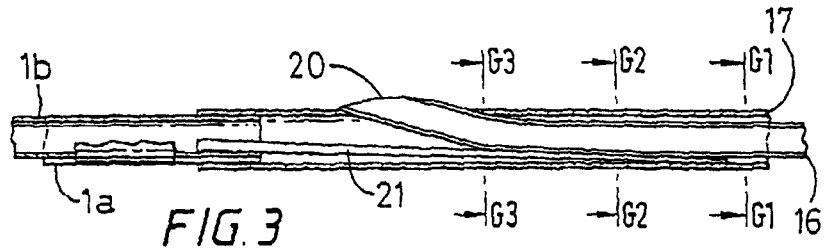
FIG. 3
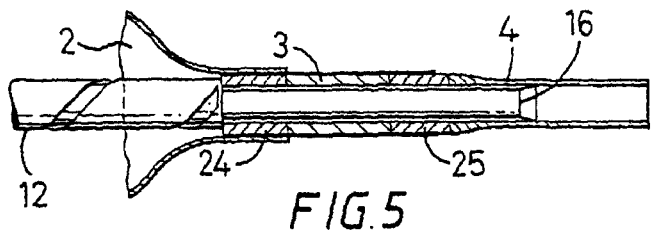
FIG. 5
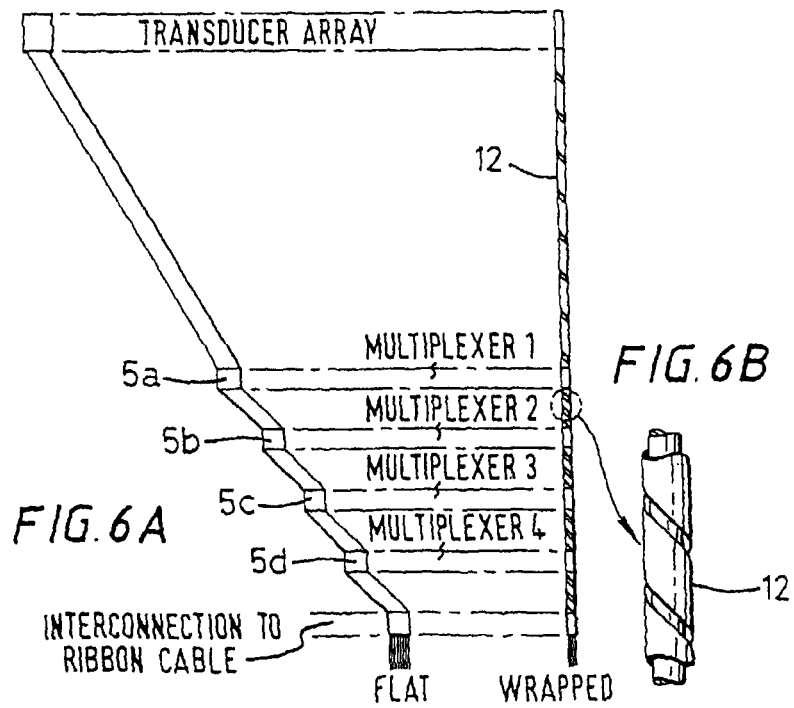
FIG. 6A
FIG. 6B

ULTRASONIC IMAGING CATHETERS

CROSS-REFERENCE TO RELATED APPLICATION

This application is a Divisional application of co-pending U.S. patent application Ser. No. 11/413,730, filed Apr. 28, 2006, which is a Continuation of U.S. patent application Ser. No. 10/333,099, filed Aug. 6, 2003, now U.S. Pat. No. 7,037, 269, which is a National Stage Entry of international patent application number PCT/GB01/03262, filed Jul. 20, 2001, which claims priority to Great Britain application number 0017674.3, filed Jul. 20, 2000, the disclosure of which is incorporated herein by reference.

This invention relates to ultrasonic imaging catheters including catheters which are combined with a balloon device.

Catheters having an ultrasonic transducer array mounted on the distal end of the catheter are known. Examples are the arrangement disclosed in the present applicant's United Kingdom patent numbers: 2 208 138; 2 212 267; 2 233 094 and 2 246 632.

Catheters fitted with a balloon which can be distended in order to press plaque in a patient's artery back into the wall of the artery (a procedure known as angioplasty) in order to increase the cross section of the artery's lumen are also well known.

In the applicant's published United Kingdom patent No. 2 325 020 there is disclosed a catheter which has the combination of an ultrasonic array at or near it's distal end combined with a balloon arrangement also carried at or near the distal end of the catheter. With the arrangement disclosed in the applicant's United Kingdom Patent No. 2 287 375 the ultrasonic imaging system includes a multiplexing arrangement which is also mounted on the catheter at or near it's distal end. This specification also discloses a method of manufacturing the transducer/multiplexer arrangement which method involves first manufacturing the arrangement in a flat configuration and then wrapping it into a cylindrical circular cross-section configuration. The transducer array and multiplexer arrangement are linearly separated from one another but electrically inter-connected by what will be referred to as a flex circuit. The transducer array is cylindrical in its final configuration as is the multiplexer arrangement, the latter consisting typically of four multiplexer units, arranged in a cylindrical box section.

The catheters to which the present invention relates are typically around one millimeter in external diameter. In the case where the catheter also incorporates an angioplast balloon and this balloon, when inflated, might typically have an external diameter of three millimeters.

There is a requirement to be able to provide the ultrasonic imaging arrangement previously described either alone or in combination with a balloon arrangement previously described in a catheter having a smaller outside diameter. More specifically, in this art the diameter of catheters is expressed in terms of units known as "french" and the present invention is concerned with providing a combined ultrasonic imaging system/balloon catheter arrangement suitable for use with a 2.4-2.9 french combination catheter. (1 French equals 0.013 inches)

There is a requirement that a stent can be pre-mounted onto the balloon and firmly attached so it does not detach.

There is a requirement that the combination catheter should smoothly negotiate a six french guide catheter and a blood vessel with a seven millimeter bend radius and it should do so without damage to the electrical circuitry and components associated with the transducer.

The following requirements/constraints apply when designing a catheter having an ultrasonic transducer array, an associated multiplexer arrangement, a balloon and a stent inserted on the balloon:

a) the balloon needs to be close to the ultrasonic array at the catheter's distal end from a visualisation point of view;

b) the multiplexer needs to be close to the ultrasonic array in order to minimise the length of the electrical connections between them and to enhance the rigidity of the distal tip of the catheter;

c) locating the mulitplexer within the balloon to meet the requirement of b) means that it needs to be electrically insulated from the saline solution used to inflate the balloon;

d) the stent needs to be securely mounted on the outside of the balloon so that it cannot be dislodged and can be radially expanded by inflation of the balloon;

e) one way to secure the stent on the outside of the balloon is to crimp it in position;

f) crimping the stent around the balloon can cause damage to the balloon and anything contained within it.

The present invention is concerned with designing the catheter in such a way that these conflicting design requirements are substantially met.

According to a first aspect of the present invention a catheter balloon specified in the first aspect above is characterised in that the multiplexer units are longitudinally separated from the transducer, and a balloon device is positioned between the most distal multiplexer and the transducer.

According to a second aspect of the present invention a catheter having an ultrasonic transducer including a plurality of multiplexer units is characterised in that the multiplexer units are longitudinally separated from one another along the length of the catheter. The catheter may also include a balloon device.

According to a third aspect of the present invention a catheter has an ultrasonic transducer arrangement located at or near its distal end, which arrangement includes a flexible circuit through which electrical power can be supplied to the transducer array, characterised in that the flexible circuit incorporates at least one helically wound section so constructed as to enhance the flexibility of that circuit and its ability to accommodate bending as the catheter is moved along a non-linear path such as an artery of a patient. The catheter may also include a balloon device.

According to a fourth aspect of the present invention the catheter arrangement specified in the first aspect above is characterised in that there are flex circuits between adjacent longitudinally separated multiplexer units, those flex circuits being characterised in that they are helically wound in order to enhance their flexibility and the overall catheter assembly's capability of negotiating bends in a non-linear path without damage being caused as a result of the bending.

According to a fifth aspect of the present invention a catheter which includes an inflatable balloon device, an ultrasonic transducer array and a flexible electrical circuit adapted to supply current to the transducer array is characterised in that at least a portion of the flexible circuit is located within the balloon device and, in use, is directly exposed to the inflating fluid introduced into the balloon device, i.e. that portion of circuit is not enclosed in a protective tube but is insulated to function when immersed.

According to a sixth aspect of the present invention a stent is crimped over the balloon, such that the crimping force does not damage the multiplexer and transducer, and the helical flex circuit limits the minimum diameter the stent is crimped to.

How the invention may be carried out will now be described by way of example only and with reference to the accompanying drawings in which:

FIG. 3 is a side elevational fragmentary view on an enlarged scale illustrating a guide wire exit to a catheter having an inner and outer body at its distal end;

Figure 1:
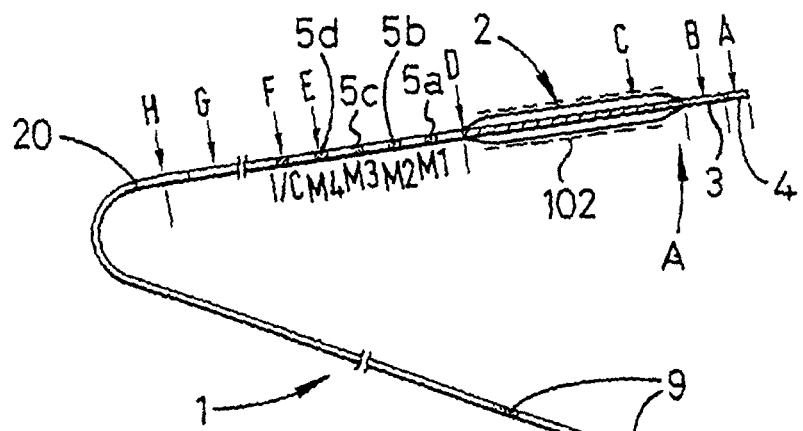
FIG. 1 is a schematic representation of a combination catheter incorporating the present invention.

FIG. 4 comprises five cross-sectional views, FIGS. 4A, 4B, 4C, 4D and 4E taken on the lines A-A, B-B, C-C, D-D and E-E respectively of FIGS. 1 and 3.

Figure 7:
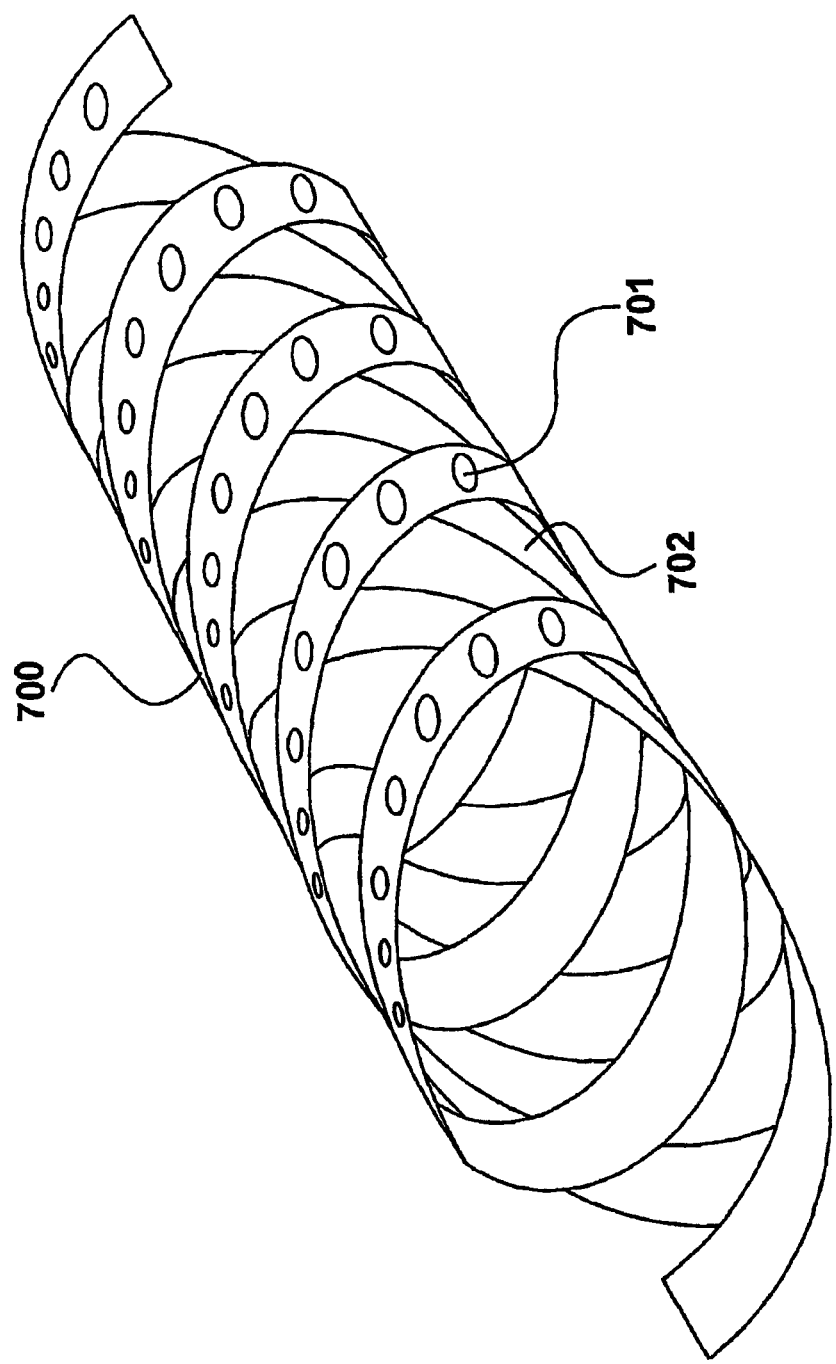

FIG. 5 is a sectional elevational view on an enlarged scale showing that portion of the catheter which comprises the transducer array adjacent the distal end of the balloon device, both balloon and transducer being located at or near the distal end of the catheter itself;

FIG. 6 comprises FIG. 6A which shows that part of the catheter which includes the transducer array, flex circuit and multiplexers when they are in the flat condition and FIG. 6B which shows the same arrangement when they are in the wrapped condition; and FIG. 7 is an enlarged prospective view of a drug loaded stent according to the present invention.

FIG. 1

This is a diagrammatic illustration of the overall catheter arrangement to which the present invention is applied.

The detailed construction is shown in the other figures of the drawings in which the same reference numerals have been used to designate the same or equivalent elements.

In FIG. 1 a catheter generally indicated at 1 has at its distal end A the combination of a balloon unit 2 and an ultrasonic annular transducer array 3, the extreme distal end of the catheter comprising a soft tip 4.

Associated with the transducer array 3 is a multiplexing arrangement indicated at 5.

At the proximal end B of the catheter there is provided a balloon inflation port 6 by which fluid (typically a saline solution 19) can be introduced through the catheter into the balloon 2 in order to inflate it in known manner.

Also at the proximal end B there is provided a connector 7 and associated strain relief device 8 by which the proximal end B of the catheter may be connected to a catheter interface module (CIM) and thus to the electronic imaging system.

At an intermediate point along its length the catheter is provided with opaque markers 9 to assist the clinician in being able to see the catheter within the patient's artery using x-ray equipment.

The ultrasonic transducer array 3 is provided with electrical power by means of a ribbon cable 22 which runs the length of the catheter, the proximal end of the ribbon cable being connected to an electrical supply and control arrangement (not shown) which itself is not part of the present invention.

The multiplexing arrangement 5 consists of a number of multiplexing units, in this case four, the functional purpose of which is to reduce the number of electrical leads which would otherwise have to be provided along the length of the catheter in order to energise the large number of transducer elements in the transducer array 3. Typically the number of elements would be sixty four. By having a multiplexing arrangement the number of electrical leads can be significantly reduced. The provision of such a multiplexing arrangement is known.

The present invention is concerned with the configuration and construction of the multiplexing arrangement and the associated flexible circuit and the relationship of the balloon device to the flexible circuit.

According to the present invention the individual multiplexing units 5a, 5b, 5c and 5d are longitudinally spaced from one another along the length of the catheter as indicated in FIG. 1, the longitudinal spacing being identified as "S".

In the arrangement of FIG. 1 the longitudinally spaced multiplexing units 5 are located immediately proximal to the balloon device 2 which in turn is proximal to the ultrasonic transducer array 3.

Mounted on the balloon is an optional stent 102 which is crimped onto the balloon. The helical flex circuit 12 acts as a limit to the crimping of the stent. The crimping operation involves application of a force which would otherwise damage components inside, but in this design the components are outside the stent region.

The construction of this distal end of the catheter is illustrated in more detail in FIGS. 2 to 5.

FIGS. 2 TO 5

Figure 2:
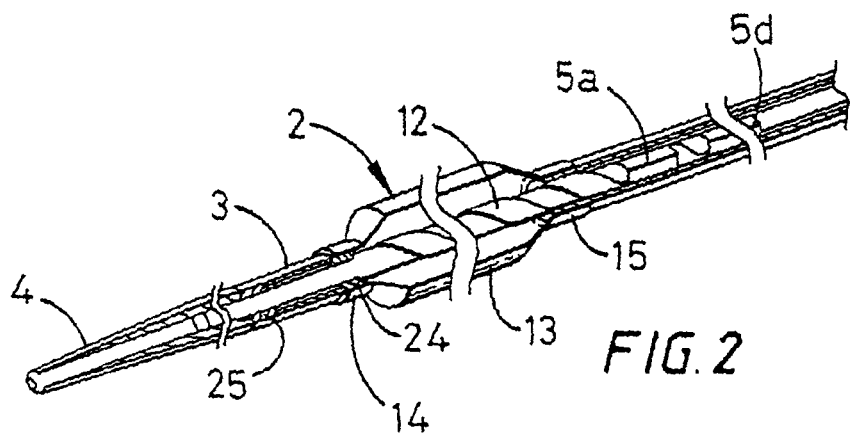
FIG. 2 is a fragmentary view on a larger scale showing a balloon device, ultrasonic transducer array and associated multiplexer arrangement forming part of the overall arrangement shown in FIG. 1.

The ultrasonic transducer array 3 consists of sixty-four individual transducer elements arranged in a cylindrical configuration, these elements being contained between a proximal ring 24 and a distal ring 25 (FIG. 2). The multiplexer units 5a, 5b, 5c and 5d are electrically connected to the transducer array 3 by means of a flexible circuit indicated at 12.

This flexible circuit 12 is arranged in a helical configuration and it passes from the transducer array 3 to the multiplexer units 5 through the balloon device 2.

The balloon device 2 comprises a flexible and expandable balloon envelope 13 which is sealed at 14 and 15 to the catheter.

That portion of the flexible circuit 12 which passes through the inside of the balloon unit 2 is insulated with a water proof coating such as Parylene™ (Specialty Coatings Ltd, Northampton) and exposed to the fluid (typically a saline solution 19) which is used to inflate the balloon envelope 13, i.e. that part of the flexible circuit 12 which is within the balloon envelope 13 is not contained within any protective tube.

At its distal end the catheter 1 consist of an inner body or tube 16 and an outer body or tube 17.

The catheter is inserted into a patient's artery after a metal guide wire 18 (see FIG. 3) has first been inserted into the artery. The catheter then in effect runs down the guide wire to bring the distal end of the catheter into the target area within the patient.

More specifically the catheter is loaded onto the proximal end of the guide wire 18 by the clinician who pushes the inner body 16 over the proximal end of the guide wire and then feeds the catheter down the guide wire. As this feeding operation occurs the guide wire 18 in effect passes outside the catheter at the guide wire exit indicated at 20, in FIG. 3, the guide wire exit 20 being formed by the end of the inner body 16.

The proximal end of the outer body 17 is sealingly secured to an outer tube 1a of the catheter which contains an inner tube 1b, typically a stainless steel hypodermic, the tubes 1a and 1b running the length of the catheter 1 up to a Y-connector 101.

A tapered metal member or wire known as a stilett 21 extends from the distal end of the inner tube 1*b* into the space between the inner and outer bodies 16 and as illustrated in FIG. 3. The purpose of the stilett 21 is to provide a support for the guide wire exit port which would otherwise have a tendency to kink.

FIG. 4

This figure comprises FIGS. 4A, 4B, 4C, 4D and 4E which are cross-sections taken on the lines G3, G2, G1, respectively in FIGS. 3, and F and E respectively in FIG. 1.

Figure 4A:
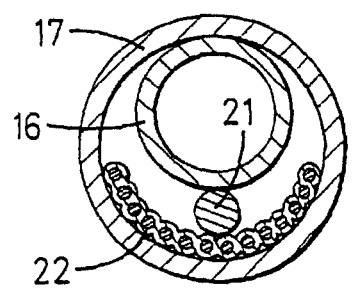
Figure 4B:
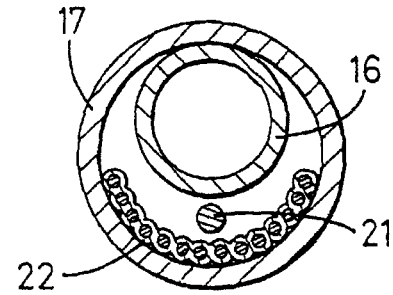
Figure 4C:
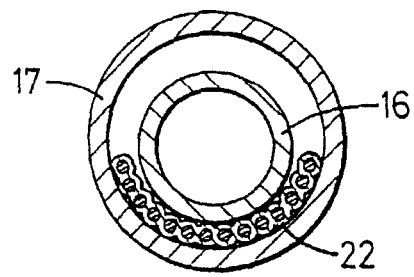
Figure 4D:
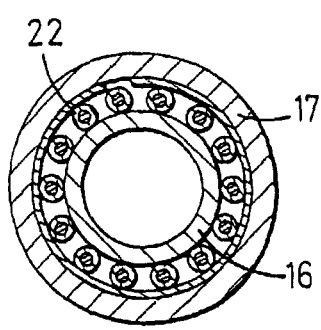

As can be seen from these cross-sections the ribbon cable 22 consists of a number of electrical leads which for most of its length are moulded together to form the unit shown in FIGS. 4A, 48 and 4C. However, at the point where it is required to connect electrically the various constituents of the ribbon cable to the four multiplexer units 5 the ribbon cable 22 is split into discreet leads as shown in FIG. 4D. These leads are then connected to the respective multiplexer units via tracks on the flex circuit.

Figure 4E:
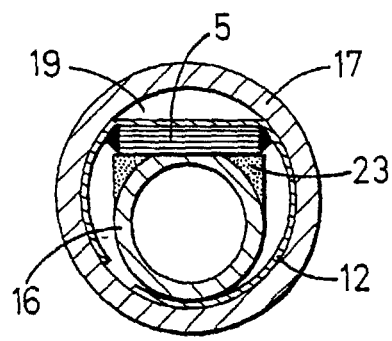

The manner in which each multiplexer unit is mounted is shown in FIG. 4E. Each multiplexer unit is secured to the inner body 16 by means of adhesive 23.

FIG. 5

This shows on a greater scale and in more detail the extreme distal end of the catheter, the same reference numerals being used to designate parts already described with reference to earlier figures.

The annular ultrasonic transducer array 3 is contained between a proximal ceramic ring 24 and a stainless steel or ceramic distal ring 25. At the distal end of the distal forming ring 25 there is the soft tip 4, which is typically made from Nylon® which is heat melted or fused onto the distal end of the inner body 16.

FIG. 6

FIG. 6A shows that part of the catheter which includes the transducer array 3 and multiplexers 5 when they are in the flat condition at an intermediate point in the manufacturing process. A more detailed disclosure of the method of manufacturing this arrangement, which involves first constructing the transducer and multiplexer assembly in the flat and then converting it into a tubular configuration is disclosed in more detail in our United Kingdom Patent No. 2 297 375

FIG. 6B shows the same arrangement as FIG. 6A but after it has been formed into the cylindrical configuration referred to earlier.

FIG. 7

The present invention also envisages a stent, such as that shown at 102 in FIG. 1, being loaded with one or more of a variety of drugs so that the drug or drugs is/are eluted or washed from the stent by the patient's blood flowing past the stent.

By having a drug loaded stent mounted on an intravascular ultrasonic imaging catheter (IVUS) it is possible for the clinician to more accurately position the stent and target the drug where it is required in order to prevent, for example, restenosis. The usual method of introducing a drug or drugs has been to simply introduce them generally into the patient's blood stream. However, this means that a large proportion of the introduced drug is in effect wasted and is not operative in the target area.

The loading of the drug or drugs onto the stent can be achieved in a number of ways.

A drug loaded surface of a stent can be achieved by using different technological approaches. Each of these approaches can be conducted in a way that the drug compound is released from the surface either in a short (hours) or an extended time frame (days). The release kinetics can be adjusted by applying specific modifications to the surface of the stent e.g. hydrophobic or hydrophilic side chains of a polymer carrier or a ceramic surface.

The following outlines four possible ways of loading the drug/drugs onto the stent.

1. Ceramic Coating

An $AlO_2$ coating (patent applications DE 19855421, DE 19910188, WO 00/25841) with porous surface can be loaded with a drug in amounts between 250 µg an 10 mg by either dipping, spraying or similar techniques. The drug dose is dependent on the nature of the target vessel and the condition of the patient and is chosen such that cell proliferation is sufficiently inhibited, while healing is not hampered. The drug can be used as an aqueous or organic solution, e.g. in DMSO, DMF and methanol. After spraying or dipping (under mild vacuum) the treated stent is dried, the procedure is repeated three to ten times. After the final drying the stent is rinsed for one minute in water or isotonic saline at room temperature and then dried again. Drug content can be analysed by standard methods (HPLC, LC-MS) after eluting or washing the compound with a suitable solvent. Release kinetics can be analysed using a standard release apparatus.

2. ePTFE Membrane: Stent Graft

Identical approach as above. The drug is absorbed into the cavities of the porous ePTFE membrane.

3. Polymeric Coating in General

Different polymers are suitable for drug loading: methacrylate-polymers, polyurethane-coatings, ePTFE-coatings. The drug can be either applied to the final surface (see above) or directly added to the polymerisation solution.

4. Mechanical Approach (FIG. 7)

The mechanical approach is based on holes 701 that have been introduced into the stent 700 struts 702 using a laser. These holes can then be filled with a drug or drugs. The hole-approach can be combined with a thin, biodegradable coating that in itself is drug loaded. After initial release from the biodegradable coating the drug-filled holes can serve for long term release of active drug. Interstices for containing the drug may be formed in other ways than by holes.

A variety of drugs that could be loaded onto the stent are listed in the following three tables, Table A, Table B and Table C. It is intended that the listed drugs should also include their derivatives.

In this example the drugs are selected to be active in three phases, Table A being Phase I, Table B being Phase II and Table C being Phase III.

Phase I is aimed at effecting vasodilation e.g. the dilation of the patient's artery. The effects are listed in the table.

Phase II is aimed at inhibiting inflammation, etc as listed at the top of Table B. Again the effects of the drugs are set out in the table.

Phase III is aimed at the inhibition of cell proliferation and again the effects of the drugs are set out in the table.

TABLE A

Phase I - Vasodilation
Drugs to be released with the first 24-72 h after stenting

| Drug name | Rationale/Effects | Priority |
| --- | --- | --- |
| Molsidomine, linsidomine, sodium nitroprusside, nitroglycerol, NO-donors in general | Release of NO leads to vasodilation, reducing the degree of procedural vessel wall damage, stimulates the growth of endothelial cells, inhibits migration and proliferation of smooth muscle cells. | 1 |
| Stimulators of the soluble guanylate cyclase like BAY 41-2272 (5-(Cyclopropyl-2-[1-(2-fluoro-benzyl)-1H-pyrazolo[3,4-n]pyridin-3-yl]-pyrimidin-4-ylamine). | SGC stimulators induce vasodilation and other NO-effects by directly activating the target enzyme of NO. | 1 |
| Hydralazine. | Causes smooth muscle cell relaxation. | 2 |
| Verapamil, dilitazem, nifedipine, nimodipine and other $Ca^{2+}$-channel blockers. | Smooth muscle cell contraction reduced by reducing intracellular $Ca^{2+}$-concentrations. | 3 |
| Captopril, enalapril, lisinopril, quinapril and other angiotensin converting enzyme inhibitors. | Reduction of the angiotensin II level leads to reduced vasoconstriction. | 1 |
| Losartan, candesartan, irbesartan, valsartan and other angiotensin II receptor antagonists. | Reduced vasoconstriction is achieved by blocking the effect of angiotensin II at its target receptor located in the vascular tissue. | 1 |

TABLE B

Phase II - Inhibition of inflammation, immunosuppression, promotion of endothelial cell growth, inhibition of cell migration.
Drugs to be released within the first 2-21 days after stenting.

| Drug name | Rationale/Effects | Priority |
| --- | --- | --- |
| Dexamethasone, Betamethasone, prednisone and other corticosteriods | Inhibition of inflammatory reactions by different effects on macrophages and monocytes, endothelial cells, basophils, fibroblasts and lymphocytes. | 1 |
| 17-beta-estradiol | Inhibition of migration and proliferation of smooth muscle cells. | |
| FK506 (Tacrolimus) | Inhibition of T-cell response, reduction of pro-inflammatory cytokine release, inhibition of smooth muscle cell proliferation | 1 |
| Cyclosporine | Inhibition of T-cell response | 3 |
| Mycophenolic acid | Inhibition of B-cell response, inhibition of smooth muscle cell proliferation | 3 |
| VEGF, VEGF-receptor activators | VEGF is a growth factor stimulating the growth of smooth muscle cells | 1 |
| Tranilast | Has shown efficacy (prevention of restenosis) in animal trials after systemic applications, inhibits keloid scarring. | 2 |
| Mefoxicam, cefebrex, vioxx and other COS-2 antagonists | Antiinflammatory effect through inhibition of cyclooxygenase 2 | 2 |
| Indomathacin, diclofenac, ibuprofen, naproxen and other COX-1 inhibitors | Antiinflammatory effect through inhibition of cyclooxygenase1, in addition platelet inhibition | 3 |
| Plasminogen activator inhibitor-1 and other serpins | Inhibits activation of prourokinase. Prourokinase promotes cellular migration by acctivating plasmin and metalloproteinases as well as other proteinases | 1 |
| Thrombin inhibitors as hirudin, hirulog, agratroban, PPACK etc. | Thrombin promotes thrombus formation but is also a strong mitogen (growth factor) | 2 |
| Interleukin-10 | Antiinflammatory cytokine that inhibits monocytes | 3 |

TABLE C

Phase III - Inhibition of cell proliferation
Drugs to be released within the first 14 days to 3 months after stenting

| Drug name | Rationale/Effects | Priority |
|---|---|---|
| Sirolimus, SDZ RAD (40-O-(2-hydroxyethyl)-rapamycin and other rapamycin drivatives | Inhibition of T-cell response, reduction of pro-inflammatory cytokine release, inhibition of smooth muscle cell proliferation | 1 |
| PDGF-antoginists | Inhibition of smooth muscle cell proliferation and migration through inhibition of PDGF-signal transduction. PDGF is a strong mitogen for smooth muscle cells. | 1 |
| Paclitaxel | Inhibition of smooth muscle cell proliferation through promotion of microtubili association | 1 |
| Cisplatin | Inhibition of smooth muscle cell proliferation through intercalation in DNA-double strand | 2 |
| Vinblastin | Inhibition of smooth muscle cell proliferation through inhibition of mitotic spindle formation | 2 |
| Mitoxantrone | Inhibition of smooth muscle cell proliferation through inhibition of DNA and RNA synthesis and inhibition of topisomerase II 1 | |
| Combretastatin A4 | Inhibition of smooth muscle cell proliferation through inhibition of mitotic spindle formation | 1 |
| Topotecan | Inhibition of smooth muscle cell proliferation through inhibition of topoisomerase I | 2 |
| Methotrexate | Inhibition of smooth muscle cell proliferation through inhibition of dihydrofolate reductase | 3 |
| Flavopiridol | Inhibition of smooth muscle cell proliferation through inhibition of cell cycle kinase | 1 |

The invention claimed is:

1. A method of manufacturing an apparatus for ultrasonic imaging, the method comprising:
   providing a catheter having a distal region;
   coupling an annular ultrasonic imaging transducer array to the distal region of the catheter such that the annular ultrasonic imaging transducer array extends annularly about a longitudinal axis of the catheter, wherein the ultrasonic imaging transducer array is fixedly secured to the distal region of the catheter in the annular configuration such that the ultrasonic imaging transducer array extends annularly about the longitudinal axis of the catheter when the distal region of the catheter extends linearly along the longitudinal axis of the catheter;
   electrically coupling a flexible circuit to the transducer array and helically winding at least a portion of the flexible circuit about the catheter, the flexible circuit configured to supply electrical power to the transducer array; and
   electrically coupling a plurality of multiplexers to the flexible circuit proximal of the transducer array such that a section of the helically wound portion of the flexible circuit is disposed between the transducer array and the plurality of multiplexers and such that the plurality of multiplexers are longitudinally separated from one another along the longitudinal axis of the catheter.

2. The method of claim 1, wherein the flexible circuit is insulated.

3. The method of claim 1, wherein the resulting apparatus has a maximum external diameter of less than about 3 Fr.

4. The method of claim 1, wherein the resulting apparatus is adapted for passing within a guiding catheter having a lumen diameter of 6 Fr or larger.

5. The method of claim 1, further comprising communicatively coupling an imaging system to the resulting apparatus.

6. A method of manufacturing an apparatus for ultrasonic imaging, the method comprising:
   providing a catheter having a distal region;
   coupling an annular ultrasonic imaging transducer array to the distal region of the catheter, wherein the ultrasonic imaging transducer array is fixedly secured to the distal region of the catheter in the annular configuration such that the ultrasonic imaging transducer array extends annularly about the longitudinal axis of the catheter when the distal region of the catheter extends linearly along the longitudinal axis of the catheter;
   electrically coupling a flexible circuit to the transducer array and helically winding at least a portion of the flexible circuit about the catheter, the flexible circuit configured to supply electrical power to the transducer array;
   electrically coupling a plurality of multiplexers to the flexible circuit proximal of the transducer array such that the helically wound portion of the flexible circuit is disposed between the transducer array and the plurality of multiplexers; and
   coupling a balloon to the catheter, wherein the balloon is coupled to the catheter proximal of the transducer array.

7. The method of claim 6, wherein the plurality of multiplexers are positioned proximal of the balloon.

8. A method of manufacturing an apparatus for ultrasonic imaging, the method comprising:
   providing a catheter having a distal region;
   coupling an ultrasonic imaging transducer array to the distal region of the catheter such that the ultrasonic transducer array extends annularly around a longitudinal axis of the catheter, wherein the ultrasonic imaging transducer array is fixedly secured to the distal region of the catheter in the annular configuration such that the ultrasonic imaging transducer array extends annularly about the longitudinal axis of the catheter when the distal region of the catheter extends linearly along the longitudinal axis of the catheter;

electrically coupling a flexible circuit to the transducer array and helically winding at least a portion of the flexible circuit about the catheter, the flexible circuit configured to supply electrical power to the transducer array;

electrically coupling at least one multiplexer to the flexible circuit; and coupling a balloon to the catheter, wherein the balloon is coupled to the catheter proximal of the transducer array;

wherein the at least one multiplexer is positioned proximal of the balloon; and wherein the at least a portion of the flexible circuit is helically wound about the catheter between the transducer array and the at least one multiplexer.

9. The method of claim 8, wherein the at least a portion of the flexible circuit is disposed within the balloon.

10. The method of claim 9, wherein the at least a portion of the flexible circuit disposed within the balloon is insulated.

11. The method of claim 8, further comprising position a stent coaxially about the balloon.

12. The method of claim 7, further comprising transitioning the transducer array from a flat configuration to a cylindrical configuration.

13. The method of claim 8, wherein electrically coupling at least one multiplexer to the flexible circuit includes electrically coupling a plurality of multiplexers to the flexible circuit.

14. The method of claim 13, wherein the plurality of multiplexers are positioned proximal of the transducer array such that the helically wound portion of the flexible circuit is disposed between the transducer array and the plurality of multiplexers.

15. The method of claim 14, wherein the balloon is positioned proximal of the transducer array and distal of the plurality of multiplexers such that at least a portion of the helically wound portion of the flexible circuit extends through the balloon.

16. The method of claim 14, wherein the plurality of multiplexers are separated from one another along the longitudinal axis of the catheter.

* * * * *